United States Patent
Koniger

(10) Patent No.: US 6,589,571 B2
(45) Date of Patent: Jul. 8, 2003

(54) METHOD FOR COMBATING SUMMER ECZEMA AND MALANDERS

(76) Inventor: Helmut Koniger, Dresselstrasse 33, Munchen (DE), 81827

( * ) Notice: Subject to any disclaimer, the term of this patent is extended or adjusted under 35 U.S.C. 154(b) by 0 days.

(21) Appl. No.: 09/961,553

(22) Filed: Sep. 20, 2001

(65) Prior Publication Data

US 2002/0068099 A1 Jun. 6, 2002

Related U.S. Application Data

(63) Continuation-in-part of application No. 09/374,754, filed on Aug. 13, 1999, now abandoned.

(30) Foreign Application Priority Data

Aug. 13, 1998 (DE) .......................... 198 55 717

(51) Int. Cl.$^7$ ........................ A61K 7/06; A61K 35/78
(52) U.S. Cl. .................. 424/725; 424/47; 424/65; 424/74; 424/828; 424/844; 424/846
(58) Field of Search ............ 424/725, 47, 65, 424/74; 514/828, 846, 844

(56) References Cited

U.S. PATENT DOCUMENTS

| 4,265,902 A | 5/1981 | Van Ewijk |
| 4,459,285 A | 7/1984 | Grollier et al. |
| 4,803,069 A | 2/1989 | Kekesi et al. |
| 5,641,481 A | 6/1997 | Koniger |

FOREIGN PATENT DOCUMENTS

| DE | 62 649 | 7/1968 |
| WO | WO 94/25041 | 11/1994 |

OTHER PUBLICATIONS

"Zeitschrift fur die Fett–, Ol–, Tensid–, Kosmetik–und Pharmaindustrie", 115 (10), 1989, p. 331–338, Table 6, p. 337.
Deutsche Apotheker Zeitung, 13 (No. 37), 1992, p. 1876.
"Drogen E–O Unter besonderer Mitarbeit von S. Greiner, G. Heubl und E. Stahl–Biskup", pp. 64–72, 1993.

Primary Examiner—Herbert J. Lilling
(74) Attorney, Agent, or Firm—Baker & Daniels

(57) ABSTRACT

The invention is concerned with a method for combating summer eczema caused by gnats of the species *Culicoides pulicolaris* and malanders in non-human mammals with a composition for external application which contains components of plants of the species Equisetum.

7 Claims, No Drawings

METHOD FOR COMBATING SUMMER ECZEMA AND MALANDERS

This application is a Continuation-In-Part application of Ser. No. 09/374,754, filed Aug. 13, 1999, now abandoned.

BACKGROUND OF THE INVENTION

1. Field of the Invention

The invention is concerned with a method for combating summer eczema and malanders (Scurf) caused by the gnats of the species *Culicoides pulicularis* as well as the cosmetic consequences with an external application of a suitable composition which contains components of plants of the genus Equisetum.

2. Background and Review of the Prior Art

The so-called summer eczema, which in the case of animals, also incorrectly called summer mange, is due to a hypersensitivity reaction of mammals (for example, horses, cattle, but also humans) to the contents of the saliva of gnats of the species *Culicoides pulicularis,* which are generally called in the vernacular in Germany "Gnietzen," "Bartmücken" (Bearded gnat), "Sandmücken" (sand flies), or "Kriebelmücken" (Columbatz gnat). These insects, which are only up to 2 mm in size, can be found in all biogeographic regions of the earth and are observed in the Northern Hemisphere, depending upon the weather and sometimes also on the region, from March–April to October–November. The gnats prefer mainly the areas of skin where there is a transition from hairy to less hairy skin. Thus, in the case of humans, it is mostly at the hairline, eyebrows, skin at the collars, sleeves, hosiery that are bitten and, in the case of mammalian animals, especially horses, near the forelock and the crown of the mane, at the croup as well as in skin areas where the hair stands up, such as the cowlick under the abdomen and on the flanks.

The reaction to the bite is highly varied; it can involve development of a rash and long-lasting itching or itching that occurs at intervals. Especially in the case of horses, they may suffer severe skin damage due to itching, including loss of hair at the mane, at the tail, and other body regions. Summer eczema is spread worldwide in the cases of horses: in Great Britain it is called "sweet itch," in Australia, "Queen's itch," and in Japan, "Kasen disease."

Malanders is a skin disease in the distal area of the limbs, widespread in hoofed animals, especially in horses and quite especially in carthorses. The disease begins as an eczema aquamosum or madidans (eczematous or regular or chapped malanders) in the fetlock joint bend, especially of the hind legs with white markings, produced by moisture, wetness, dirt during thawing, paths with droppings, and can develop to Dermatitis verrucosa with the formation of cauliflower-like growths with foul-smelling secretion. Other symptoms are the development of little blisters and cracks, painful reddening and swelling of the pasterns, strong wetness of the transfer folds which frequently become cracked, sores under sticky hairs, with strong thickening of the skin (callused malanders). After healing of the cracks, welts and ulcers, mostly severe peeling occurs (squamous eczema) and bulging skin sclerosis.

Gangrenous malanders develop as a result of additional anaerobic infection. It progresses very typically in an acute case: painful, hot ulcer with redness in the fetlock joint (erythema), lymphangitic swelling of the entire area, especially upward, lameness and fever. Suddenly, at a certain location, a bluish color appears which will partly become insensitive, dry and rough, the hairs stand on end and after a few days, gangrenous dying of a piece of the skin, together with the surrounding cell tissue occurs, followed by discharge of pus and rejection of the discolored, leather-like part (rejecting malanders-literal).

Equisetum, especially the species *Equisetum arvense* (also called "field horse tail"), in the vernacular also tinweed, since this species, which is widespread as a weed, was used earlier for the cleaning of tin equipment, and *Equisetum hiemale* were presumably used as healing plants in ancient times, but in recent times, Equisetum was brought back to memory above all by Kneipp.

The active ingredients of the weed *Equisetum arvense* are silicic acid (partly in the soluble form), equisetonin (saponin), a bitter substance, small amounts of 3-methoxypyridine, nicotine, palustrin, isoquercitrin, galueteolin, dimethylsulfone, resin, fat, aconitic acid and other acids, vitamin C, enzymes, and polyenoic acids.

External application of Equisetum has also been known recently. DD-62 640 uses an extract of herba Equiseti together with skin-care and hair-care agents which contain organ preparations, to compensate for the strong odor of organ preparations. The use of Equisetum components in the form of pulverized plants as an antiperspirant is described in DE-A-32 07 005. *Equisetum arvense* in the form of an aqueous or glycol extract in soaps, fats, oils, is mentioned as a skin-firming agent in the Zeitshcrift für die Fett-, Öl-, Tensid-, Kosmetik- und Pharmaindustrie, 115(10), 1989, p. 331–338, Table 6, p. 338. As a decoction (10 g/1000 mL), Equiseta herbs (*Equisetum arvense*), obtained standard approval of the Bundes-gesundheitsamt (Federal Health Office) for use in bandages for supporting treatment of poorly healing wounds (Deutsche Apotheker Zeitung, 132 (No. 37), 1992, p. 1876).

DEA-A-43 14 131 discloses the external use of Equisetum in psoriasis. DE-A-43 18 655 discloses the external use of Equisetum in burns, sun allergies, allergic contact skin diseases, dandruff, pain the muscles, tendons, ligaments, joints and neuralgic pain, pain caused by gout, as well as in the case of fungus in the nails, bad skin, pimples and acne.

Lavender oil is used mainly in the area of cosmetics as an odor-correcting agent, and it is supposed to have a calming influence.

In DE-A 42 37 551, a synergistically acting composition of Equisetum and lavender is disclosed as a means to combat dermatomycoses, of their pathogens as well as seating and body odor.

U.S. Pat. No. 4,265,902 describes a systemic administration of allantoin to horses which suffer eczema at the tail and mane.

The expression "treatment" means amelioration of the symptoms and/or healing of the symptoms of summer eczema and malanders, the prevention of the related diseases and/or cosmetic symptoms, where possible post-treatment with the composition administered according to the invention should also be included.

SUMMARY OF THE INVENTION

The task of the invention is to provide a method for combating summer eczema caused in humans and mammalian animals by the gnat species *Culicoides pulicularis* as well as the malanders that occurs in hoofed animals.

This task is solved by a method for therapeutic treatment of a mammal which suffers from summer eczema caused by gnats of the species *Culicoides pulicularis* and malanders, especially from the cosmetic consequences or is at risk to suffer from it, which includes the following: application of a certain composition which contains components of plants of the genus Equisetum to mammals which suffer from summer eczema caused by gnats of the species *Culicoides pulicularis* or is at risk to suffer from it.

Surprisingly, it was found that the composition used according to the method of the invention ameliorates or eliminates within a short period of time the itching of summer eczema and the chafing that is caused by the itching in horses, and, in addition to that, it stops summer eczema and heals it. The animals become quiet again and the hair is growing again in the places where it fell out.

The species *Equisetum arvense* or *Equisetum hiemale* are preferred in the area of healing and cosmetics.

DETAILED DESCRIPTION OF THE INVENTION

As a starting material for the composition used for the method according to the invention, which contains components of the plants of the genus Equisetum, numerous pharmaceutical preparations of the plant are possible. For example, one can use powdered, finely cut, freeze-dried, spray-dried components or a juice or an oily, pasty, syrup-lie preparation, preferably in an aqueous-alcoholic extract of the plant. These preparations are either available commercially or their production can be derived by the expert (see, for example, Paul Heinz List and Peter C. Schmidt, "Technology of Plant Drug Preparation," Wissenschaftliche Verlagsgellschaft mbH, Stuttgart, 1984).

Particularly preferred as a starting material containing the active ingredient *Equisetum arvense* for the compositions to be used in the method of the present invention is a horsetail herb fluid extract 1:1 (v/v) with the extracting agent being 30% (v/v) aqueous ethanol which is commercially available from Chemische Fabrik Dr. Hetterich K G, Fuerth, Germany (in the following: Extracutum Equiseti fluidum 1:1). This extract is prepared as follows:

The drug in the form of air-dried (in the shadow) horsetail herb (*Equiseti herba*) is cut into pieces of 6 cm×6 cm and is filled into a high-grade steel percolator of a suitable size. The extraction medium is prepared by mixing 50 parts by eight of 96% (v/v) ethanol with 150 parts by weight of extraction grade water (which corresponds to 30% (v/v) aqueous ethanol). The exhaustive percolation of the drug by means of the extraction medium is conducted at ambient temperature and ambient pressure 2 to 3 parts by weight of extraction medium, depending upon the amount of the charge and the speed of percolation are required for 1 part by weight of drug. The fluid extract is then stored at below or at 15° C. for 5 days to sediment suspended and clouding particles. The extract is filtered, and concentrated below or at 50° C. in a high vacuum to the end concentration of 1 part extracted drug to 1 part extraction medium.

Another preferred starting material for the composition used in the inventive method is the juice which is squeezed from the fresh herb of *Equisetum arvense*.

These preparations can represent partly the composition of the invention as such, for example, the juice from Equisetum, which is naturally also a composition, can be applied as such onto a skin area to be treated. However, as a rule, the pharmaceutical preparations are brought into a galenic form, which is suitable for external application, with the aid of one or several carriers, and these preparations can be powders, salves, creams, gels, lotions, emulsions, solutions, for example, applicable as a spray and sprays with propellant (aerosols). The usual carriers and additives known to the expert are used. The preparation of such galenic forms are known in the field and have been widely published in the literature (see, for example, Remington's Pharmaceutical Sciences, Mack Publishing Company, Easton, Pa., 1990).

The preparation which is suitable for external application may also contain liposomes with or without the enclosed active ingredient. The method of addition of liposomes and the inclusion of active ingredients into liposomes is known to the expert and does not have to be explained here further.

In this invention, highly hypoallergenic preparations in the form of a cream, lotion, salve or a spray with or without propellant are especially preferred.

In such galenic forms, the Equisetum components (optionally without carriers) are usually contained in a concentration of 0.001 to 99 weight %, more commonly at 0.01 to 50 weight %, preferably from 0.01 to 20 weight % and most preferably from 1 to 10 weight % based on the composition, with the remainder being carriers and other additives and optionally other active ingredients, however, with the exclusion of essential oils, in particular, lavender oil.

The examples given below explain the invention further and should not be considered to be limiting the scope of the invention.

Cream. The cream used in the examples was a commercially available (from VEMA GmbH & Co. KG, Neusaess, Germany), active-ingredient-free cream base into which 3.5% by weight, based on the total weight of the cream, of the above Extractum Equiseti fluidum 1:1 was mixed in the usual manner.

EXAMPLE 1

A horse suffering from chronic malanders with strong incrustation in the fetlock joint bend of the hind legs was treated with the above-mentioned Equisetum-containing cream by applying it to the afflicted region and massaging it in well three times a day. Already after ca. one week of treatment, a marked improvement of the elasticity of the skin and a decrease of the crust was observed. At the end of ca. three weeks, the malanders were completely healed.

EXAMPLE 2

Two horses with severe malanders in the fetlock joint bend region of all four legs were treated with the Equisetum-containing cream as described in Example 1. The disease subsided rapidly and healthy skin regenerated. This success was surprising, since the animals had before been treated unsuccessfully with several other preparations.

EXAMPLE 3

Two studs and a mare suffered from malanders in the fetlock joint bends, the studs at the forelegs and the mare at all four legs. After treatment with the Equisetum-containing cream as described in Example 1 for two weeks, a complete healing was achieved with the studs. A marked improvement was seen with the mare.

EXAMPLE 4

A stud showed a ca. 7 cm diameter circular hairless spot near the dorsal tail base. This spot showed a keratose and itching due to summer eczema. The hairlessness was a result of the stud's chafing of the buttocks. After treatment for several days with the Equisetum-containing cream as described in Example 1, the chafing had ceased and after two weeks of treatment, hair grew again.

I claim:

1. A method for the therapeutic treatment of a non-human mammal which suffers from summer eczema caused by a gnat of the species *Culicoides pulicularis* or from malanders, as well as for the prevention thereof and treatment of cosmetic consequences thereof, wherein said non-human mammal is treated by applying a composition designed for external application, which contains components of plants of the genus Equisetum and does not contain any added essential oils, and wherein said components consist of an extract from *Equisetum arvense* obtainable by a process comprising the steps of (a) cutting dried herb of *Equisetum arvense* (*Equiseti herba*) into pieces of about 6 cm×6 cm and placing said pieces in a percolator; (b) preparing an extraction medium by mixing 1 part by weight of 96% (v/v) ethanol with 3 parts by weight of water; (c) exhaustively percolating said pieces with said extraction medium, to obtain an extract of *Equisetum arvense*; (d) storing said extract for 5 days at or below 15° C. (e) filtering said extract; and (f) concentrating this extract at or below a temperature of 50° C. in a high vacuum.

2. The method of claim 1, wherein said components in said composition are present in a concentration of from 0.001 to 50% by weight, based on the weight of the composition, the remainder being one or more excipients for external application and optionally one or more additional active ingredients with the exception of essential oils.

3. The method of claim 1, wherein said composition is a cream or a lotion, wherein said components are present in a concentration of from 1 to 10% by weight, based on the weight of the composition.

4. The method of claim 1, wherein said composition is a spray with or without a propellant gas.

5. The method of claim 1, wherein said extract is present in said composition in a concentration, based on Equisetum content without extraction medium, of from 0.001 to 50% by weight, based on the weight of the composition, the remainder being one or more excipients for the external application and optionally one or more additional active ingredients with the exclusion of added essential oils.

6. The method of claim 1, wherein said composition is a cream or a lotion, wherein said extract is present in a concentration, based on Equisetum content without extraction medium, of from 1 to 10% by weight, based on the weight of the composition.

7. The method of claim 5, wherein said composition is a spray with or without a propellant gas.

* * * * *